(12) United States Patent
Jansen et al.

(10) Patent No.: US 10,280,439 B2
(45) Date of Patent: May 7, 2019

(54) FERMENTATION PROCESS FOR PRODUCTION OF A DICARBOXYLIC ACID USING FUNGAL CELLS

(71) Applicants: DSM IP ASSETS B.V., Heerlen (NL); ROQUETTE FRÈRES SA, Lestrem (FR)

(72) Inventors: Mickel Leonardus August Jansen, Echt (NL); René Verwaal, Echt (NL); Laurent Segueilha, Lestrem (FR); Mélanie Louchart, Lestrem (FR); Tania Veiga Dos Inocentes, Lestrem (FR)

(73) Assignees: DSM IP ASSESTS B.V., Heerlen (NL); ROQUETTE FRERES SA, Lestrem (FR)

(*) Notice: Subject to any disclaimer, the term of this patent is extended or adjusted under 35 U.S.C. 154(b) by 0 days.

(21) Appl. No.: 14/997,530

(22) PCT Filed: Jul. 18, 2014

(86) PCT No.: PCT/EP2014/065552
§ 371 (c)(1),
(2) Date: Jan. 16, 2016

(87) PCT Pub. No.: WO2015/007902
PCT Pub. Date: Jan. 22, 2015

(65) Prior Publication Data
US 2016/0194670 A1 Jul. 7, 2016

(30) Foreign Application Priority Data
Jul. 18, 2013 (EP) .................................. 13177052

(51) Int. Cl.
*C12P 7/44* (2006.01)
*C12P 7/46* (2006.01)
*C12N 1/18* (2006.01)

(52) U.S. Cl.
CPC .................. *C12P 7/44* (2013.01); *C12N 1/18* (2013.01); *C12P 7/46* (2013.01)

(58) Field of Classification Search
None
See application file for complete search history.

(56) References Cited

U.S. PATENT DOCUMENTS

| 4,477,569 A * | 10/1984 | Schneider ............... C12P 7/065 435/161 |
| 5,573,931 A | 11/1996 | Guettler et al. |
| 6,596,521 B1 | 7/2003 | Chang et al. |

FOREIGN PATENT DOCUMENTS

| CN | 101215583 A | 7/2008 |
| WO | 2010003728 A1 | 1/2010 |
| WO | 2013004670 A1 | 1/2013 |

OTHER PUBLICATIONS

International Search Report and Written Opinion dated Oct. 8, 2014, issued in PCT/EP2014/065552.
Xuefei, B et al., "[Recycle of spent cells from anaerpbic succinate fermentation]." Sheng wu gong cheng xue bao [Chinese Journal of Biotechnology] 2010;26(9):1276-1280—XP002717864.
Du Preez, JC "Process parameters and environmental factors affecting D-xylose fermentation by yeasts." Enzyme Microb Technol. 1994;16(11):944-956.

* cited by examiner

*Primary Examiner* — Christian L Fronda
(74) *Attorney, Agent, or Firm* — McBee Moore Woodward & Vanik IP, LLC; Susan McBee; Chester Moore

(57) ABSTRACT

The present invention relates to a method for a dicarboxylic acid, which method comprises fermenting fungal cells in a vessel comprising a suitable fermentation medium, wherein a least a portion of the fungal cells are reused in the presence of a vitamin and/or a trace element.

15 Claims, 4 Drawing Sheets

Specification includes a Sequence Listing.

FERMENTATION PROCESS FOR PRODUCTION OF A DICARBOXYLIC ACID USING FUNGAL CELLS

CROSS REFERENCE TO RELATED APPLICATIONS

This application is a § 371 National Stage Application of PCT/EP2014/065552, filed 18 Jul. 2014 which claims priority to EP 13177052.1, filed 18 Jul. 2013.

BACKGROUND

Field of the Invention

The present invention relates to a process for the production of a dicarboxylic acid.

Description of Related Art

Dicarboxylic acids such as malic acid, fumaric acid and succinic acid, are important compounds which are used in the food industry for the preparation and preservation of food, in the medical industry for the formulation of medical products, building blocks in (bio)polymers and other industrial uses. To meet the increasing need for dicarboxylic acids, more efficient and cost effective production methods are being developed.

Several processes for the production of a dicarboxylic acid are known. Traditionally, dicarboxylic acids are made by fermentation of bacteria at neutral pH, for example described in U.S. Pat. No. 5,573,931. Also other microorganisms like yeasts have been employed for the production of dicarboxylic acids at low pH, which has the advantage of producing the acid directly (WO2010/003728).

In order to realize an economically viable process, fast and efficient production of the dicarboxylic acid is required. The required efficiency puts an upper limit on the amount of biomass which can be used in a fermentation process. This has an impact on the productivity, which current processes suffer from. This can be solved by re-using of biomass, thereby allowing higher biomass concentrations. This technique as such to increase fermentation rates is well described for many applications like ethanol production (Cyzewski et al., 1977).

However, for the production of dicarboxylic acids, a negative impact on the inherent activity has been observed in a second fermentation run. This means that a significant part of the re-used biomass is not producing anymore, thereby hampering the implementation of processes incorporating cell recycling.

The present disclosure aims to provide an improved method for the fermentative production of a dicarboxylic acid which overcomes the disadvantage of non-productive biomass when use in fermentation outlined above.

SUMMARY

The present invention relates to a process for producing a dicarboxylic acid. The process comprises fermenting a fungal strain in a vessel, the vessel comprising a suitable fermentation medium. The process is carried out in such a way that at least a portion of the cells is reused, i.e. recycled. The cells may be recycled back into the original vessel or into a second vessel. Critically, the reuse of a portion of the fungal cells is carried out in the presence of a vitamin and/or a trace element.

During the standard production of a dicarboxylic acid via fermentation of a fungal strain, a decrease in the specific productivity (qp) is typically seen. Similarly, recycled cells grown in the same medium also exhibit a decrease in the specific productivity (qp). Surprisingly, however, we have found that supplementing the medium with vitamins and trace elements when reuse takes place results in the full recovery of the qp, reaching the same levels as in the initial fermentation. A higher KPi may be observed: qp reduction and higher Yps.

According to the invention, there is thus provided a process for the preparation of a dicarboxylic acid, which method comprises fermenting fungal cells in a vessel comprising a suitable fermentation medium, wherein a least a portion of the fungal cells are reused in the presence of a vitamin and/or a trace element.

DETAILED DESCRIPTION OF A PREFERRED EMBODIMENT

Figure 1:
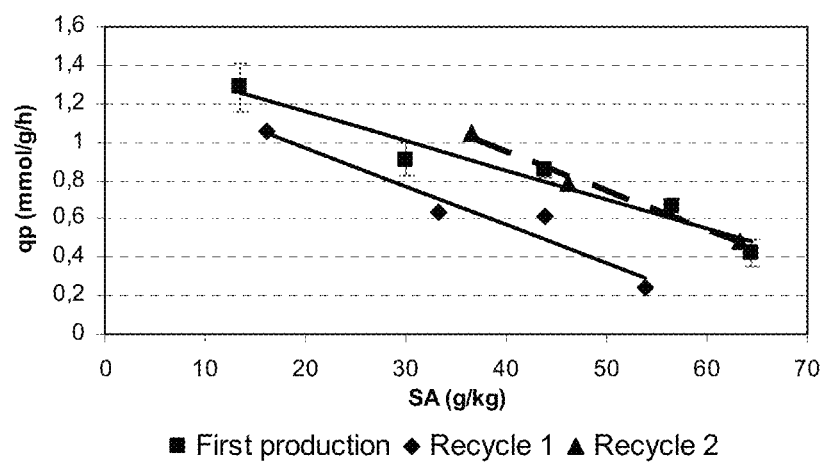
FIG. 1 shows succinic acid productivity (normalized per biomass) before and after different cell recycles.

Throughout the present specification and the accompanying claims, the words "comprise", "include" and "having" and variations such as "comprises", "comprising", "includes" and "including" are to be interpreted inclusively. That is, these words are intended to convey the possible inclusion of other elements or integers not specifically recited, where the context allows.

The articles "a" and an are used herein to refer to one or to more than one (i.e. to one or at least one) of the grammatical object of the article. By way of example, "an element" may mean one element or more than one element.

The invention relates to a process for the production of a dicarboxylic acid. The terms "dicarboxylic acid" and "dicarboxylate", such as "succinic acid, or malic acid" and "succinate and malate", have the same meaning herein and are used interchangeably, the first being the hydrogenated form of the latter.

In the process fungal cells are fermented in a vessel comprising a suitable fermentation medium. The term fermenting, fermentation or fermented and the like as used herein refers to the microbial production of compounds, here dicarboxylic acids from carbohydrates.

Preferably, the fermentation product is a dicarboxylic acid, preferably malic acid, fumaric acid or succinic acid or adipic acid, preferably succinic acid.

Preferred embodiments of the process for producing a fermentation product are further as defined herein for the process for the production of dicarboxylic acid.

Critically, in the invention, a least a portion of the fungal cells used in the fermentation are reused, that is to say a portion of the fungal cells are recycled, in the presence of a vitamin and/or a trace element.

The present invention relates to a process for the production of a dicarboxylic acid. The process comprises fermenting a fungal strain in a vessel, the vessel comprising a suitable fermentation medium. The process is carried out in such a way that at least a portion of the cells are reused. The cells may be recycled back into the original vessel or into a second vessel. Critically, the reuse of the fungal cells is carried out in the presence of a vitamin and/or a trace element.

For the purposes of this invention, a vitamin is an organic compound required by an organism, in this case a fungal strain, as a vital nutrient in limited amounts. An organic chemical compound (or related set of compounds) may be considered a vitamin when it cannot be synthesized in sufficient quantities by the organism (fungal strain).

A vitamin for use in the invention is typically a B vitamin (or vitamin form the vitamin B complex or the like). Examples of a B vitamin which are suitable for use in the invention include a Vitamin $B_1$ such as thiamine, a vitamin $B_2$ (such as riboflavin), a Vitamin $B_3$ (such as niacin or niacinamide), a Vitamin $B_5$ (such a pantothenic acid), a Vitamin $B_6$ (such as pyroxidinem pyridoxal or pyridoxamine or pyridoxine hydrochloride), a Vitamin $B_7$ (such as biotin), a Vitamin $B_8$ (such as myo-inositol) a Vitamin $B_9$ (such as folic acid), a Vitamin $B_{12}$ (such as various cobalamins, for example cyanocobalamin) or a vitamin $B_x$ (such as p-aminobenzoic acid). Any one of these or a mixture of these may be used in cell reuse according to the invention.

A vitamin is typically used in the invention at an average concentration of less than 1000 parts per million measured in atomic count or less than 1000 micrograms per gram. A vitamin is typically used in the invention at an average concentration of at least about 1 part per million measured in atomic count or at least about 1 microgram per gram.

For the purposes of this invention, a trace element is a mineral that is needed only in very minute quantities for the proper growth, development, and physiology of an organism, in this case a fungal strain. A trace element herein is a chemical element required by a living organism, in this case a fungal strain, other than the four elements carbon, hydrogen, nitrogen and oxygen present in common organic molecules.

Typically, a trace element is not a chemical element which may be considered a macronutrient or macromineral. The chemical elements considered macronutrients are those typically consumed by organisms in the greatest quantities, i.e. carbon, hydrogen, nitrogen, oxygen, phosphorus and sulphur. Calcium, salt (sodium and chloride, magnesium and potassium (along with phosphorus and sulfur) may be added to the list of macronutrients since they are required in large quantities compared to other vitamins and elements.

Accordingly, the elements which may be considered trace elements may include iron, cobalt, copper, zinc, molybdenum, iodine, selenium, boron, chromium, arsenic and silicon. However, a macronutrient may be considered a trace element for the purposes of this invention. Any one of the trace elements or any mixture of any of these may be used in cell reuse according to the invention.

A trace element is typically used in the invention at an average concentration of less than 1000 parts per million measured in atomic count or less than 1000 micrograms per gram. A vitamin is typically used in the invention at an average concentration of at least about 1 part per million measured in atomic count or at least about 1 microgram per gram.

In the process, cells from the fermentation are withdrawn and resused, i.e. they are recycled. This means that they are reintroduced into the same fermentation vessel and/or introduced into a second fermentation vessel (containing a suitable fermentation medium). In every case, however, the reuse is carried out in in the presence of a vitamin and/or a trace element. That is to say, the fermentation medium is supplemented with a vitamin and/or a trace element when the fungal cells are reused.

As set out above, the method of the invention comprises cell reuse carried out in the presence of a vitamin and/or a trace element. In other words, the fermentation medium into which the recycled cells are introduced is supplemented with a vitamin and/or a trace element. Typically, the fermentation medium is supplemented with a mixture of vitamins and trace elements.

The medium into which recycled cells are introduced is typically one which will allow at least some growth of the recycled cells. The medium into which the recycled cells are introduced may comprise a nitrogen source, such an ammonium. It may also be preferably to add additional iron source.

Multiple recycles/recycle steps may be carried out. For example two, three, four, five or more recycle steps may be used in a process for the production of a dicarboxylic acid according to the process of the invention.

A suitable inoculum concentration in a recycle step may be determined by one skilled in the art. A suitable inoculum concentration may be from about 10 g/L to about 50 g/L, for example about 15 g/L to about 20 g/L. A suitable inoculation concentration may be about the same as the final biomass concentration in the production culture.

The process for the production of dicarboxylic acid according to the present invention may be carried out in any suitable mode, such as a batch, fed-batch, continuous mode or any suitable combination of these fermentation modes. Preferably, the process for the production of dicarboxylic acid according to the present invention is carried out in a fed-batch mode or continuous mode.

Methods for carrying out cell recycling in all of these fermentation modes are well-known to the skilled person.

Methods for reusing cells can be distinguished from each other on the basis of the location at which the cells are separated from the product stream.

Such biomass separation can take place outside or inside the fermentation vessel. If separation of the cells occurs outside the fermentation vessel, this can be done by gravitational forces such as e.g. centrifugation or decantation or by mechanical forces such as e.g. filtration techniques. If the separation of cells takes place inside the fermentation vessel this may be carried out by e.g. settling or (self-)flocculation of the cells after which the clear upper layer can be removed and the remaining cells be re-used.

A batch fermentation is defined herein as a fermentation wherein all nutrients are added at the start of a fermentation.

A fed-batch fermentation is a batch fermentation wherein the nutrients are added during the fermentation. Products in a batch and fed-batch fermentation may be harvested at a suitable moment, for instance when one or more nutrients are exhausted A continuous fermentation is a fermentation wherein nutrients are continuously added to the fermentation and wherein products are continuously removed from the fermentation.

In one embodiment fermenting the yeast in the process of the invention is carried out under carbohydrate limiting conditions. As used herein, carbohydrate limiting conditions are defined as maintaining the carbohydrate concentration below 10 g/l, for example about 5 g/l.

The process for the production of dicarboxylic acid according to the present invention may be carried out in any suitable volume and scale, preferably on an industrial scale. Industrial scale is defined herein as a volume of at least 10, or 100 liters, preferably at least 1 cubic meter, preferably at least 10, or 100 cubic meters, preferably at least 1000 cubic meters, usually below 10,000 cubic meters.

Fermenting the fungal cells in the process of the invention may be carried out in any suitable fermentation medium comprising a suitable nitrogen source, carbohydrate and other nutrients required for growth and production of a dicarboxylic acid in the process of the invention. A suitable carbohydrate in the fermentation process according to the invention may be glucose, galactose, xylose, arabinose, sucrose, or maltose.

In one embodiment, the fermentation process is carried out under a partial $CO_2$ pressure of between 5% and 60%, preferably about 50%.

The pH during the process for the production of dicarboxylic acid usually lowers during the production of the dicarboxylic acid. Preferably, the pH in the process for the production of dicarboxylic acid ranges between 1 and 5, preferably between 1.5 and 4.5, more preferably between 2 and 4.

In another preferred embodiment the process according to the present invention comprises a step of preculturing the fungal cells under aerobic conditions in the presence of a carbohydrate. Preferably, the fermenting of the fungal cells during preculturing is carried out at a pH of between 4 and 6. Preferably, the carbohydrate during preculturing is a non-repressing carbohydrate, preferably galactose. It has been found advantageous to preculture fungal cells on a non-repressing carbohydrate, since this prevents glucose repression occurring, which may negatively influence the amount of biomass produced. In addition, it has been found that a step of preculturing fungal cells under aerobic conditions results in a higher biomass yield and a faster growth. Preferably, the preculturing is carried out in batch mode.

A propagation step for producing increased biomass is typically carried out, preferably under carbohydrate limiting conditions.

A process for producing a dicarboxylic acid may be carried out at any suitable temperature. A suitable temperature may for instance be between about 10 and about 40 degrees Celsius, for instance between about 15 and about 30 degrees Celsius.

A suitable fungal cell for use in a process as disclosed herein may belong to any suitable genera, for example *Saccharomyces, Aspergillus, Penicillium, Pichia, Kluyveromyces, Yarrowia, Candida, Hansenula, Humicola, Issatchenkia, Torulaspora, Trichosporon, Brettanomyces, Rhizopus, Zygosaccharomyces, Pachysolen* or *Yamadazyma*. A fungal cell suitable for use in the process of the invention may be a yeast, for example one belonging to one of the genera *Schizosaccharomyces, Saccharomyces, Yarrowia, Candida, Pichia, Kluyveromyces, Issatchenkia* or *Zygosaccharomyces*. More preferably, the yeast is a *Saccharomyces cerevisiae, Saccharomyces uvarum, Saccharomyces bayanus, Yarrowia lipolytica, Candida sonorensis, Schizosaccharomyces pombe, Pichia stipidis, Kluyveromyces marxianus, K. lactis, K. thermotolerans, Issatchenkia orientalis* or *Zygosaccharomyces bailii*.

A fungal cell in a process as disclosed herein may be any suitable wild type or recombinant or genetically modified fungal cell, in particular a recombinant or genetically modified yeast cell.

A genetically modified fungal cell may comprise a genetic modification of a gene selected from the group consisting of a gene encoding a pyruvate carboxylase, a phosphoenolpyruvate carboxykinase, a malate dehydrogenase, a fumarase, a fumarate reductase, an isocitrate lyase, a malate synthase and a dicarboxylic acid transporter.

Thus, a genetically modified yeast cell suitable for use in the process of the invention, may comprise any suitable genetic modifications, such as deletions or disruptions, and insertions of homologous or heterologous nucleotides sequences. A yeast cell suitable for use in the process of the invention may be genetically modified or transformed with nucleotide sequences that encode homologous and/or heterologous enzymes that catalyse reactions in the cell resulting in an increased flux towards a dicarboxylic acid such malic acid, fumaric acid and/or succinic acid. It may for example be favourable to introduce and/or overexpress nucleotide sequences encoding i) a malate dehydrogenase which catalyses the conversion from OAA to malic acid; ii) a fumarase, which catalyses the conversion of malic acid to fumaric acid; or iii) a fumarate reductase that catalyses the conversion of fumaric acid to succinic acid, depending on the dicarboxylic acid to be produced.

Thus, in the invention a genetically modified yeast cell may be used. Preferably, a yeast cell used in the process according to the present invention comprises genetic modifications according to the preferred embodiments as described herein below.

A recombinant fungal cell may comprise a genetic modification with a pyruvate carboxylase (PYC), that catalyses the reaction from pyruvate to oxaloacetate (EC 6.4.1.1). The pyruvate carboxylase may for instance be active in the cytosol upon expression of the gene. For instance the fungal cell overexpresses a pyruvate carboxylase, for instance an endogenous or homologous pyruvate carboxylase is overexpressed.

Preferably the genetically modified yeast cell expresses a nucleotide sequence encoding a phosphoenolpyruvate (PEP) carboxykinase in the cytosol. Preferably a nucleotide sequence encoding a phosphoenolpyruvate (PEP) carboxykinase is overexpressed. The PEP carboxykinase (EC 4.1.1.49) preferably is a heterologous enzyme, preferably derived from bacteria, more preferably the enzyme having PEP carboxykinase activity is derived from *Escherichia coli, Mannheimia* sp., *Actinobacillus* sp., or *Anaerobiospirillum* sp., more preferably *Mannheimia succiniciproducens*. A gene encoding a PEP carboxykinase may be overexpressed and may be expressed and active in the cytosol of a fungal cell. Preferably, a yeast cell according to the present invention is genetically modified with a PEP carboxykinase which has at least 80, 85, 90, 95, 99 or 100% sequence identity with amino acid sequence of SEQ ID NO: 1.

In one embodiment a fungal cell is further genetically modified with a gene encoding a malate dehydrogenase (MDH) active in the cytosol upon expression of the gene. Cytosolic expression may be obtained by deletion of a peroxisomal targeting signal. The malate dehydrogenase may be overexpressed. A cytosolic MDH may be any suitable homologous or heterologous malate dehydrogenase, catalyzing the reaction from oxaloacetate to malate (EC 1.1.1.37), for instance derived from *S. cerevisiae*.

Preferably, the MDH is *S. cerevisiae* MDH2 which has been modified such that it is not inactivated in the presence of glucose and is active in the cytosol. It is known that the transcription of MDH2 is repressed and Mdh2p is degraded upon addition of glucose to glucose-starved cells. Mdh2p deleted for the first 12 amino-terminal amino acids is less-susceptible for glucose-induced degradation (Minard and McAlister-Henn, J. Biol Chem. 1992 Aug. 25; 267(24): 17458-64). Preferably, a yeast cell according to the present invention comprises a nucleotide sequence encoding a malate dehydrogenase that has at least 70%, preferably at least 75, 80, 85, 90, 92, 94, 95, 96, 97, 98, 99% or 100% sequence identity with the amino acid sequence of SEQ ID NO: 4.

In another embodiment a fungal cell of the present disclosure is further genetically modified with a gene encoding a fumarase, that catalyses the reaction from malic acid to fumaric acid (EC 4.2.1.2). A gene encoding fumarase may be derived from any suitable origin, preferably from microbial origin, for instance a yeast such as *Saccharomyces* or a filamentous fungus, such *Rhizopus oryzae*, or a bacterium such a *Escherichia coli*. A fungal cell of the present disclosure may overexpress a nucleotide sequence encoding a fumarase. The fumarase may be active in the cytosol upon expression of the nucleotide sequence, for instance by deleting a peroxisomal targeting signal. It was found that cytosolic activity of a fumarase resulted in a high productivity of a dicarboxylic acid by the fungal cell.

Preferably, a yeast in the process according to the present invention overexpresses a nucleotide sequence encoding a fumarase that has at least 70%, preferably at least 75, 80, 85, 90, 92, 94, 95, 96, 97, 98, or 99% or 100% sequence identity with the amino acid sequence of SEQ ID NO: 3.

In another embodiment the fungal cell is genetically modified with any suitable heterologous or homologous gene encoding a NAD(H)-dependent fumarate reductase, catalyzing the reaction from fumarate to succinate (EC 1.3.1.6). The NADH-dependent fumarate reductase may be a heterologous enzyme, which may be derived from any suitable origin, for instance bacteria, fungi, protozoa or plants. A fungal cell of the present disclosure comprises a heterologous NAD(H)-dependent fumarate reductase, preferably derived from a *Trypanosoma* sp, for instance a *Trypanosoma brucei*. In one embodiment the NAD(H)-dependent fumarate reductase is expressed and active in the cytosol, for instance by deleting a peroxisomal targeting signal. The fungal cell may overexpress a gene encoding a NAD(H)-dependent fumarate reductase.

Preferably, a yeast cell according to the present invention is genetically modified with a NAD(H)-dependent fumarate reductase, which has at least 80, 85, 90, 95, 99 or 100% sequence identity with the amino acid sequence of SEQ ID NO: 2.

In another embodiment, a genetically modified yeast in the process according to the invention expresses a nucleotide sequence encoding a dicarboxylic acid transporter protein, preferably a malic acid transporter protein (MAE) in the cytosol. Preferably the dicarboxylic acid transporter protein is overexpressed. A dicarboxylic acid transporter protein may be any suitable homologous or heterologous protein. Preferably the dicarboxylic acid transporter protein is a heterologous protein. A dicarboxylic acid transporter protein may be derived from any suitable organism, preferably from yeast or fungi such as *Schizosaccharomyces pombe* or *Aspergillus niger*. Preferably, a dicarboxylic acid transporter protein is a malic acid transporter protein (MAE) which has at least 80, 85, 90, 95 or 99% or 100% sequence identity with the amino acid sequence of SEQ ID NO: 5.

A genetically modified fungal cell may further comprise a genetic modification with a gene encoding an isocitrate lyase (EC 4.1.3.1), which may be any suitable heterologous or homologous enzyme. The isocitrate lyase may for instance be obtained from *Kluyveromyces lactis* or *Escherichia coli*.

A genetically modified fungal cell may further comprise as genetic modification with a malate synthase (EC 2.3.3.9). The malate synthase may be overexpressed and/or active in the cytosol, for instance by deletion of a peroxisomal targeting signal. In the event the malate synthase is a *S. cerevisiae* malate synthase, for instance the native malate synthase is altered by the deletion of the SKL carboxy-terminal sequence.

In another embodiment, a recombinant fungal cell in the process for producing a dicarboxylic acid disclosed herein comprises a disruption of a gene encoding an enzyme of the ethanol fermentation pathway. A gene encoding an enzyme of an ethanol fermentation pathway, may be pyruvate decarboxylase (EC 4.1.1.1), catalyzing the reaction from pyruvate to acetaldehyde, or alcohol dehydrogenase (EC 1.1.1.1), catalyzing the reaction from acetaldehyde to ethanol. Preferably, a fungal cell in the process as disclosed herein comprises a disruption of one, two or more genes encoding an alcohol dehydrogenase. In the event the fungal cell is a yeast, e.g. *S. cerevisiae*, the yeast preferably comprises a disruption of an alcohol dehydrogenase gene adh1 and/or adh2.

Alternatively or in addition, the yeast in the process of the invention comprises at least one gene encoding glycerol-3-phosphate dehydrogenase which is not functional. A glycerol-3-phosphate dehydrogenase gene that is not functional is used herein to describe a eukaryotic cell, which comprises a reduced glycerol-3-phosphate dehydrogenase activity, for instance by mutation, disruption, or deletion of the gene encoding glycerol-3-phosphate dehydrogenase, resulting in a decreased formation of glycerol as compared to a wild-type cell.

Preferably, a genetically modified yeast in the process according to the present invention overexpresses a nucleotide sequence encoding a PEP carboxykinase, a nucleotide sequence encoding a malate dehydrogenase, a nucleotide sequence encoding a fumarase, a nucleotide sequence encoding a NAD(H) dependent fumarate reductase, and/or a nucleotide sequence encoding a malic acid transporter protein, preferably wherein the enzymes are active in the cytosol. Preferred embodiments of the enzymes are as described herein above.

Cytosolic expression of the enzymes described above may be obtained by deletion of a peroxisomal or mitochondrial targeting signal. The presence of a peroxisomal or mitochondrial targeting signal may for instance be determined by the method disclosed by Schluter et al., Nucleid Acid Research 2007, 35, D815-D822.

As used herein, a genetically modified yeast according to the present invention is defined as a cell which contains, or is transformed or genetically modified with or a nucleotide sequence or polypeptide that does not naturally occur in the yeast cell, or it contains additional copy or copies of an endogenous nucleic acid sequence, or it contains a deletion or disruption of an endogenous or homlogous nucleotide sequence. A wild-type eukaryotic cell is herein defined as the parental cell of the recombinant cell.

The term "homologous" when used to indicate the relation between a given (recombinant) nucleic acid or polypeptide molecule and a given host organism or host cell, is understood to mean that in nature the nucleic acid or polypeptide molecule is produced by a host cell or organism of the same species, preferably of the same variety or strain.

The term "heterologous" when used with respect to a nucleic acid (DNA or RNA) or protein refers to a nucleic acid or protein that does not occur naturally as part of the organism, cell, genome or DNA or RNA sequence in which it is present, or that is found in a cell or location or locations in the genome or DNA or RNA sequence that differ from that in which it is found in nature. Heterologous nucleic acids or proteins are not endogenous to the cell into which it is introduced, but have been obtained from another cell or synthetically or recombinantly produced.

Sequence identity is herein defined as a relationship between two or more amino acid (polypeptide or protein) sequences or two or more nucleic acid (polynucleotide) sequences, as determined by comparing the sequences. Usually, sequence identities or similarities are compared over the whole length of the sequences compared. In the art, "identity" also means the degree of sequence relatedness between amino acid or nucleic acid sequences, as the case may be, as determined by the match between strings of such sequences.

Preferred methods to determine identity are designed to give the largest match between the sequences tested. Methods to determine identity and similarity are codified in publicly available computer programs. Preferred computer program methods to determine identity and similarity between two sequences include BLASTP and BLASTN, publicly available from NCBI and other sources (BLAST Manual, Altschul, S., et al., NCBI NLM NIH Bethesda, Md. 20894). Preferred parameters for amino acid sequences comparison using BLASTP are gap open 11.0, gap extend 1, Blosum 62 matrix.

The term "nucleic acid" as used herein, includes reference to a deoxyribonucleotide or ribonucleotide polymer, i.e. a polynucleotide, in either single- or double-stranded form, and unless otherwise limited, encompasses known analogues having the essential nature of natural nucleotides in that they hybridize to single-stranded nucleic acids in a manner similar to naturally occurring nucleotides (e.g., peptide nucleic acids). A polynucleotide can be full-length or a subsequence of a native or heterologous structural or regulatory gene. Unless otherwise indicated, the term includes reference to the specified sequence as well as the complementary sequence thereof.

There are various means available in the art for overexpression of nucleotide sequences encoding enzymes in a yeast in the process of the invention. In particular, a nucleotide sequence encoding an enzyme may be overexpressed by increasing the copy number of the gene coding for the enzyme in the cell, e.g. by integrating additional copies of the gene in the cell's genome, by expressing the gene from a centromeric vector, from an episomal multicopy expression vector or by introducing an (episomal) expression vector that comprises multiple copies of the gene. Preferably, overexpression of the enzyme according to the invention is achieved with a (strong) constitutive promoter.

Suitable promoters in fungal cells are known to the skilled man in the art. Suitable promotors may be, but are not limited to, TDH1, TDH3, GAL7, GAL10, GAL1, CYC1, HIS3, ADH1, PH05, ADC1, ACT1, TRP1, URA3, LEU2, ENO1, TPI1, AOX1, PGL, GPDA and GAPDH. Other suitable promoters include PDC1, GPD1, PGK1, and TEF1.

A gene encoding an enzyme may be ligated into a nucleic acid construct, for instance a plasmid, such as a low copy plasmid or a high copy plasmid. The fungal cell according to the present invention may comprise a single copy, but preferably comprises multiple copies of a gene, for instance by multiple copies of a nucleotide construct. A nucleic acid construct may be maintained episomally and thus comprises a sequence for autonomous replication, such as an autonomously replicating sequence and a centromere (Sikorski and Hieter, 1989, Genetics 122, 19-27). A suitable episomal nucleic acid construct may e.g. be based on the yeast 2p or pKD1 plasmids (Gleer et al., 1991, Biotechnology 9: 968-975), or the AMA plasmids (Fierro et al., 1995, Curr. Genet. 29:482-489). Alternatively, each nucleic acid construct may be integrated in one or more copies into the genome of the fungal cell. Integration into the cell's genome may occur at random by non-homologous recombination but preferably, the nucleic acid construct may be integrated into the cell's genome by homologous recombination as is well known in the art.

In a preferred embodiment the process for the production of a dicarboxylic acid further comprises recovering the dicarboxylic acid. Recovery of the dicarboxylic acid may be carried out by any suitable method.

In one embodiment, a dicarboxylic acid that is produced in a process as disclosed herein is recovered from the fermentation medium. Recovery of a dicarboxylic acid may be carried out by any suitable method known in the art, for instance by crystallization, ammonium precipitation, ion exchange technology, centrifugation or filtration or any suitable combination of these methods.

In a preferred embodiment, the recovery of dicarboxylic acid comprises crystallizing the dicarboxylic acid and forming dicarboxylic acid crystals. Preferably, the crystallizing of dicarboxylic acid comprises removing part of the fermentation medium, preferably by evaporation, to obtain a concentrated medium.

In a preferred embodiment the process according to the present invention comprises recovering a dicarboxylic acid which is a succinic acid and wherein the recovering comprises crystallizing succinic acid from an aqueous solution having a pH of between 1 and 5 and comprising succinic acid, comprising evaporating part of the aqueous solution to obtain a concentrated solution, lowering the temperature of the concentrated solution to a value of between 5 and 35 degrees Celsius, wherein succinic acid crystals are formed. Preferably, the crystallizing comprises bringing the temperature of the concentrated medium to a temperature of between 10 and 30 degrees Celsius, preferably between 15 and 25 degrees Celsius. Preferably, the fermentation medium has a pH of between 1.5 and 4.5, preferably between 2 and 4.

It has been found that crystallizing succinic acid at higher temperatures such as between 10 and 30 degrees Celsius results in succinic acid crystals with a lower amount of impurities such as organic acid, protein, color and/or odor, than succinic acid crystals that were crystallized at a low temperature of below 10 degrees.

Another advantage of crystallizing succinic acid at a higher temperature is that it requires a lower amount of energy for cooling the aqueous solution as compared to a process wherein crystallizing succinic acid is carried out below 10 or 5 degrees Celsius, resulting in a more economical and sustainable process.

Preferably, the crystallizing of succinic acid comprises a step of washing the succinic acid crystals. Succinic acid may be crystallized directly from the fermentation medium having a pH of between 1 and 5 to a purity of at least 90% w/w, preferably at least 95, 96, 97, or at least 98%, or 99 to 100% w/w.

Preferably, the recovery of the dicarboxylic acid, preferably succinic acid, comprises removing the biomass from the fermentation medium and crystallizing the dicarboxylic acid, preferably crystallizing as described herein above. Preferably, the removing of biomass is carried out by filtration.

In a preferred embodiment, the process for the production of a dicarboxylic acid further comprises using the dicarboxylic acid in an industrial process. An industrial process for a dicarboxylic acid may be the application as a cosmetic additive, deicing agent, food additive or as a building block for (bio)polymers.

In a preferred embodiment, the fermentation medium comprises an amount of succinic acid of between 1 and 150 g/l, preferably between 5 and 100 g/l, more preferably between 10 and 80 g/l or between 15 and 60 g/l of succinic acid.

In another aspect the present invention relates to a process for crystallizing succinic acid from an aqueous solution having a pH of between 1 and 5 and comprising succinic acid, comprising removing part of the aqueous solution by evaporation to obtain a concentrated solution, and bringing the temperature of the concentrated solution to a value of between 10 and 30 degrees Celsius, wherein succinic acid crystals are formed. Preferably, the crystallizing comprises bringing the temperature of the concentrated solution between 15 and 25 degrees Celsius, preferably between 18 and 22 degrees Celsius. Preferably, the aqueous solution has a pH of between 1.5 and 4.5, preferably between 2 and 4. The aqueous solution may be any suitable solution comprising succinic acid. The aqueous solution may comprise soluble constituents and insoluble constituents and, such as (fragments of) microbial cells, protein, plant biomass lignocellulose, cellulose and the like. Preferably the aqueous solution is a fermentation medium, preferably a fermentation medium obtainable by a process for the production of a dicarboxylic acid as described herein.

Standard genetic techniques, such as overexpression of enzymes in the host cells, genetic modification of host cells, or hybridisation techniques, are known methods in the art, such as described in Sambrook and Russel (2001) "Molecular Cloning: A Laboratory Manual ($3^{rd}$ edition), Cold Spring Harbor Laboratory, *Cold Spring Harbor Laboratory Press*, or F. Ausubel et al, eds., "Current protocols in molecular biology", Green Publishing and Wiley Interscience, New York (1987). Methods for transformation, genetic modification etc of fungal host cells are known from e.g. EP-A-0 635 574, WO 98/46772, WO 99/60102 and WO 00/37671, WO90/14423, EP-A-0481008, EP-A-0635 574 and U.S. Pat. No. 6,265,186.

A reference herein to a patent document or other matter which is given as prior art is not to be taken as an admission that that document or matter was known or that the information it contains was part of the common general knowledge as at the priority date of any of the claims.

The disclosure of each reference set forth herein is incorporated herein by reference in its entirety.

The invention is further illustrated by the Examples:

EXAMPLES

Example 1: Effect of Different Media Composition on Succinic Acid Production by Yeast after Recycling of the Biomass The yeast strain SUC-632 constructed as described in WO2013/004670, was cultivated in shake-flask (150 ml) for 3 days at 30° C. and 110 rpm. The medium was based on Verduyn et al. (Verduyn C, Postma E, Scheffers W A, Van Dijken J P. Yeast, 1992 July; 8(7):501-517), with modifications in the carbon and nitrogen sources, as described herein below.

TABLE 1

Preculture medium composition

| Raw material | | Concentration (g/L) |
|---|---|---|
| Galactose | $C_6H_{12}O_6 \cdot H_2O$ | 20.0 |
| Urea | $(NH_2)_2CO$ | 2.3 |
| Potassiumdihydrogen phosphate | $KH_2PO_4$ | 3.0 |
| Magnesium sulphate | $MgSO_4 \cdot 7H_2O$ | 0.5 |
| Trace element solution[a] | | 1 |
| Vitamin solution[b] | | 1 |

| Component | Formula | Concentration (g/kg) |
|---|---|---|
| EDTA | $C_{10}H_{14}N_2Na_2O_8 \cdot 2H_2O$ | 15.00 |
| Zincsulphate·7H$_2$O | $ZnSO_4 \cdot 7H_2O$ | 4.50 |
| Manganesechloride·2H$_2$O | $MnCl_2 \cdot 2H_2O$ | 0.84 |
| Cobalt (II) chloride·6H$_2$O | $CoCl_2 \cdot 6H_2O$ | 0.30 |
| Copper (II) sulphate·5H$_2$O | $CuSO_4 \cdot 5H_2O$ | 0.30 |
| Sodium molybdenum·2H$_2$O | $Na_2MoO_4 \cdot 2H_2O$ | 0.40 |
| Calciumchloride·2H$_2$O | $CaCl_2 \cdot 2H_2O$ | 4.50 |
| Ironsulphate·7H$_2$O | $FeSO_4 \cdot 7H_2O$ | 3.00 |
| Boric acid | $H_3BO_3$ | 1.00 |
| Potassium iodide | KI | 0.10 |
| Biotin (D-) | $C_{10}H_{16}N_2O_3S$ | 0.05 |
| Ca D(+) panthothenate | $C_{18}H_{32}CaN_2O_{10}$ | 1.00 |
| Nicotinic acid | $C_6H_5NO_2$ | 1.00 |
| Myo-inositol | $C_6H_{12}O_6$ | 25.00 |
| Thiamine chloride hydrochloride | $C_{12}H_{18}Cl_2N_4OS \cdot xH_2O$ | 1.00 |
| Pyridoxol hydrochloride | $C_8H_{12}ClNO_3$ | 1.00 |
| p-aminobenzoic acid | $C_7H_7NO_2$ | 0.20 |

[a]Trace elements solution
[b]Vitamin solution

Subsequently, the content of the shake-flask was transferred into a seed fermenter (starting volume 10 L), which contained the following medium:

TABLE 2

Medium composition of the seed fermenter

| Raw material | | Concentration (g/L) |
|---|---|---|
| Ammonium sulphate | $(NH_4)_2SO_4$ | 1.0 |
| Potassium dihydrogen phosphate | $KH_2PO_4$ | 10 |
| Magnesium sulphate | $MgSO_4 \cdot 7H_2O$ | 5.0 |
| Trace element solution | | 8.0 |
| Vitamin solution | | 8.0 |

The pH was controlled at 5.0 by addition of ammonia (28 wt %). Temperature was controlled at 30° C. pO$_2$ was controlled at 20% by adjusting the stirrer speed. Glucose concentration was kept limited by controlled feed to the fermenter (exponent of 0.1 was applied).

After 70 hours of fermentation, 1.5 L of culture broth of the seed fermenter was transferred to a production fermenter (starting volume 15 L), with the following medium:

TABLE 3

Medium composition of the production fermenter

| Raw material | | Concentration (g/L) |
|---|---|---|
| Urea | $(NH_2)_2CO$ | 1.0 |
| Potassium dihydrogen phosphate | $KH_2PO_4$ | 1.5 |
| Magnesium sulphate | $MgSO_4 \cdot 7H_2O$ | 0.5 |
| Iron sulphate·7H$_2$O | $FeSO_4 \cdot 7H_2O$ | 0.006 |

TABLE 3-continued

Medium composition of the production fermenter

| Raw material | | Concentration (g/L) |
|---|---|---|
| Chalk | $CaCO_3$ | 4 |
| Biotin | $C_{10}H_{16}N_2O_3S$ | 0.001 |

No pH control was applied, as the added $CaCO_3$ initially buffered the medium at the pH of 5-5.5. As result of natural acidification the pH dropped towards 3 at the end of fermentation. Temperature was controlled at 30° C. Glucose concentration was kept limited by controlled feed to the fermenter (0-24 h: 3.2 g/L/h; >24 h: 2.1 g/L/h. When necessary, these rates were adjusted accordingly).

After 48 hours 2.25 L sample was withdrawn from the production fermenter, centrifuged at 4500 rpm for 1 min and re-introduced to a new fermenter (2 L volume). Different media were tested (Table 4), with the same conditions as in the production fermentation being applied and the glucose feed rates adapted to the amount of biomass present (5.7 g/L/h).

TABLE 4

Media composition cell recycle fermentations (standard medium)

| Raw material | Recycle 1 Concentration (g/L) | Recycle 2 Concentration (g/L) |
|---|---|---|
| Urea | 1.0 | 1.0 |
| Potassium dihydrogen phosphate | 1.5 | 1.5 |
| Magnesium sulphate | 0.5 | 0.5 |
| Iron sulphate•$7H_2O$ | 0.006 | 0.003 |
| Trace element solution | | 1.0 |
| Vitamin solution | | 1.0 |

During the standard production of succinic acid a decrease in the specific productivity qp, expressed as g of succinic acid produced per g of biomass present per h, is observed (FIG. 1). Similarly, recycled cells grown in the same medium exhibit a decrease in the specific productivity qp. Surprisingly, supplementing the medium with vitamins and trace elements results in the full recovery of the qp, reaching the same levels as in the production fermentation.

Example 2: Effect of Inoculum Concentration

In this Example, the procedure as set out in Example 1 was followed, but using the protocol for the recycling phase and solutions shown at the end of the Examples. Different inoculum concentrations were used in the recycling fermenters, with the same, double or triple concentration of the initial biomass concentration of the production culture. ($OD(T_0)=30$, $OD(T_0)=60$ and $OD(T_0)=90$, respectively).

The medium utilized for the production and recycling cultures was the same. The feed rate was proportionally calculated accordingly to the 30 OD.

Figure 2:
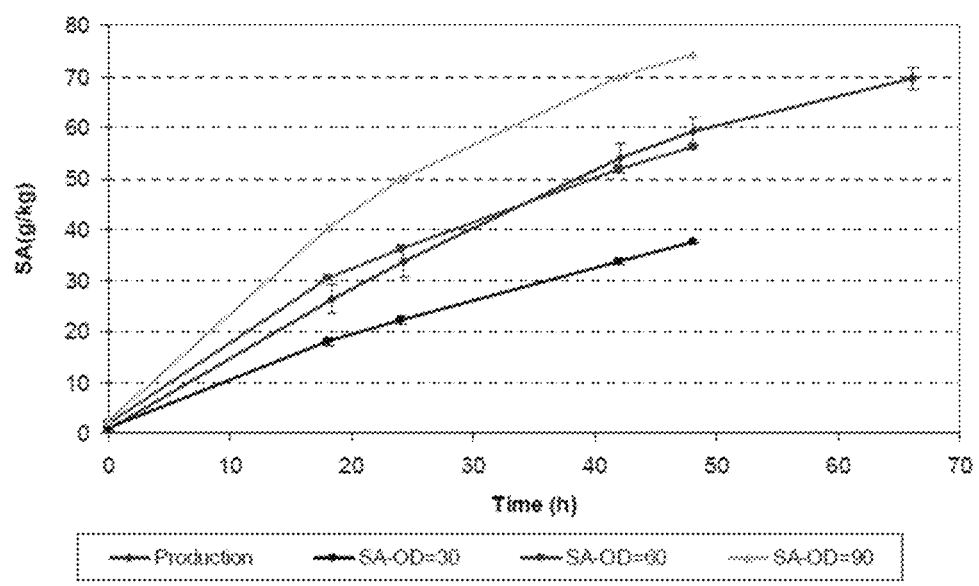
FIG. 2 shows evolution of succinic acid concentrations in the recycling cultures with the different initial biomass concentration. The production culture was used as reference.

The results are shown in Table 5 and FIG. 2. From the values obtained from this set of experiments, it is clear that an initial concentration of 15 g/l (OD=90) is the most beneficial for the recycling runs. Furthermore, this concentration equals the final biomass concentration in the production culture.

TABLE 5

Effect of the inoculum concentration after 48 h culture during the recycling phase of SUC-632

| Protocol | [SA] (g/kg) | Biomass concentration (g/kg) | Produced biomass (g/kg Al) | Overall yield Y/glc (%) | Specific production rate qp (g/g/h) | Volumic productivity rp (g/kg/h) | Kpi (DSP Yield = 0.9) |
|---|---|---|---|---|---|---|---|
| | 59.1 ± 2.7 | 13.7 ± 0.2 | 13.6 ± 0.4 | 48.9 ± 1.1 | 0.089 ± 0.005 | 1.23 ± 0.05 | 0.67 ± 0.01 |
| OD ($T_0$) = 30 DW ($T_0$) = 6 g/l Glu Feed Rate: 1.95 g/l/h | 37.6 ± 0.4 | 11.1 ± 0.4 | 5.3 ± 0.4 | 45.3 ± 0.6 | 0.071 ± 0.003 | 0.79 ± 0.007 | 0.525 ± 0.007 |
| OD ($T_0$) = 60 DW ($T_0$) = 12 g/l Glu Feed Rate: 3.78 g/l/h | 56.1 | 13.7 | 4.0 | 46.3 | 0.085 | 1.17 | 0.63 |
| OD ($T_0$) = 90 DW ($T_0$) = 15 g/l Glu Feed Rate: 4.88 g/l/h | 74.3 | 21.4 | 9.3 | 49.3 | 0.072 | 1.55 | 0.73 |

Example 3: Effect of Medium Composition

In this Example, the procedure as set out in Example 1 was followed, but using the protocol for the recycling phase and solutions shown at the end of the Examples.

The medium composition in the recycling cultures was studied in order to verify its impact on cell fitness. Based on the data obtained for the recycling cultures with different inoculum concentrations, see Example 2, the results of this study are presented for the cultures inoculated with 20 g/l of biomass, the condition most favorable.

Figure 3:
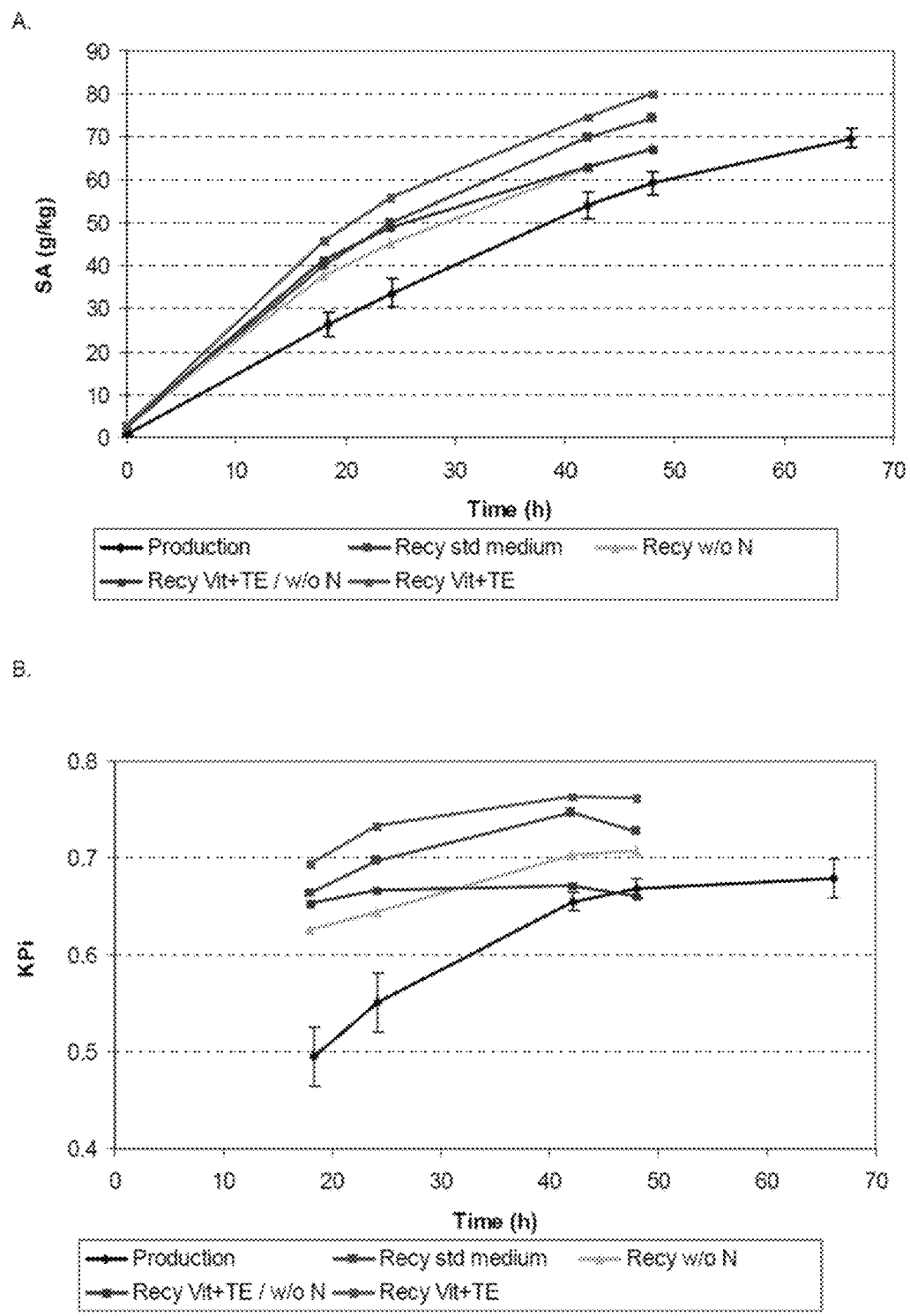
FIG. 3 shows characterization of the media composition impact on the recycling cultures. The production culture was used as reference. A. Amount of succinic acid produced; B. KPI achieved.

The results are shown in Table 6 and FIG. 3. The production of succinic acid and the KPI achieved are higher when a defined complete media was used (STD+complete vits/OE solutions (see Table)+Fe×1). The biomass viability in this condition was higher than 85%.

The absence of ammonium as nitrogen source has a negative impact in succinic acid production. This suggests that for the cells to have a similar physiology in production and recycling cultures, it may be necessary to allow at least some cell growth. This study was also performed for cultures inoculated with a lower biomass (data not shown) with similar results.

TABLE 6

Effect of the medium composition after 48 h during the recycling phase of a SUC-632 culture, inoculated with 20 g/l (OD = 90) of biomass.

| Protocol | [SA] (g/kg) | Biomass concentration (g/kg) | Produced biomass (g/kg Al) | Overall yield Y/glc (%) | Specific production rate qp (g/g/h) | Volumic productivity rp (g/kg/h) | Kpi (DSP Yield = 0.9) |
|---|---|---|---|---|---|---|---|
| | 59.1 ± 2.7 | 13.7 ± 0.2 | 13.6 ± 0.4 | 48.9 ± 1.1 | 0.089 ± 0.005 | 1.23 ± 0.05 | 0.67 ± 0.01 |
| STD medium Feed Rate: 4.88 g/l/h | 74.3 | 21.4 | 9.3 | 49.3 | 0.072 | 1.55 | 0.73 |
| STD medium w/o urea Feed Rate: 5.3 g/l/h | 67.4 | 16.8 | 0.2 | 49.8 | 0.084 | 1.40 | 0.71 |
| STD medium + complete vits/OE solutions + Fe X 1 w/o urea Feed Rate: 5.95 g/l/h | 67.1 | 16.0 | 0.6 | 44.5 | 0.087 | 1.40 | 0.66 |
| STD medium + complete vits/OE solutions + Fe X 1 Feed Rate: 5.6 g/l/h | 80.1 ± 0.4 | 22.2 ± 0.9 | 8.0 ± 1.8 | 51.2 ± 1.8 | 0.076 ± 0.004 | 1.67 ± 0.007 | 0.76 ± 0.01 |

Example 4: The Effect of Multiple Recycling Steps

In this Example, the procedure as set out in Example 1 was followed, but using the protocol for the recycling phase and solutions shown at the end of the Examples.

Figure 4:
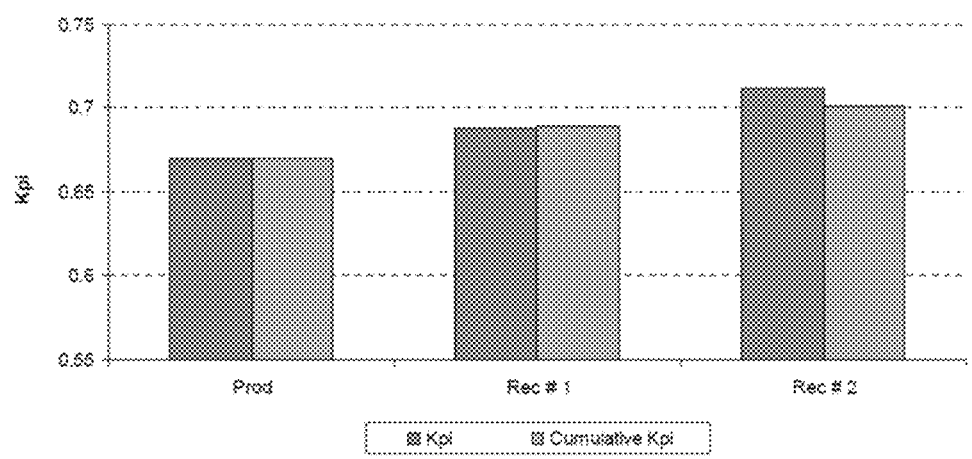
FIG. 4 shows comparison of the KPI value for the individual fermentations and its cumulative value, i.e. taking into account the fermentations ran previously.

The success of biomass recycling cultures led to the implementation of multiple recycling steps. The same protocol was used as in the first recycling, with the exception that the biomass was harvest from the previous recycling culture (instead the production culture). Once more, based on the results already shown for the inoculum concentration and medium composition for the recycling cultures, the best conditions were applied, i.e. 20 g/l inoculum and a defined complete media (see Table 7 and FIG. 4).

TABLE 7

Effect of the number of recyclings after 48 h during of a SUC-632 culture, inoculated with 20 g/l (OD = 90) of biomass and grown in a define complete media. First row shows standard production culture and fourth row show average prod + rec

| Protocol | [SA] (g/kg) | Biomass concentration (g/kg) | Produced biomass (g/kg Al) | Overall yield Y/glc (%) | Specific production rate qp (g/g/h) | Volumic productivity rp (g/kg/h) | Kpi (DSP Yield = 0.9) |
|---|---|---|---|---|---|---|---|
| | 59.1 ± 2.7 | 13.7 ± 0.2 | 13.6 ± 0.4 | 48.9 ± 1.1 | 0.089 ± 0.005 | 1.23 ± 0.05 | 0.67 ± 0.01 |
| First recycling Feed Rate: 5.72 g/l/h | 71 | 19.6 | 8.8 | 46 | 0.075 | 1.48 | 0.69 |
| Second recycling Feed Rate: 5.78 g/l/h | 71.9 | 23.6 | 9.7 | 48.5 | 0.063 | 1.50 | 0.71 |
| | 69.2 | | | 48.6 | | 1.33 | 0.70 |

The KPI value in the second recycling culture is higher than the production or first recycling step (0.71 versus 0.67 e 0.69, respectively). Therefore, the cumulative KPI value in the overall process (production+1 step recycling+2 step recycling) increases with the number of recycling steps.

Protocol and Media Compositions for Examples 2 to 4

Recycling Protocol

1: take a sterile sample of the production phase (750 ml for 30 OD in the recycling fermenter);
2: centrifuge sterile bottles at 4200 rpm during 1 minute
3: remove from supernatant
4: resuspend the biomass with some sterile water
5: add the suspended biomass in the recycling fermenter Media Composition STD Medium

| | | concentration g/L |
|---|---|---|
| urée | $CH_4N_2O$ | 1 |
| potassium dihydrogen phosphate | $KH_2PO_4$ | 1.5 |

-continued

| | | concentration g/L |
|---|---|---|
| magnesium sulphate | $MgSO_4 \cdot 7H_2O$ | 0.5 |
| antimousse | erol 18 | 0.1 ml/l |
| iron solution | sol mère | 2 ml/l |

Heat sterilized together in demi water

After Sterilization

|  |  |  |
|---|---|---|
| biotin solution | sol mère | 1 ml/l |
| CaCO$_3$ |  | 4 g/l |

Standard Medium w/o Urea

|  |  | concentration g/L |
|---|---|---|
| potassium dihydrogen phosphate | KH$_2$PO$_4$ | 1.5 |
| magnesium sulphate | MgSO$_4$•7H$_2$O | 0.5 |
| antimousse | erol 18 | 0.1 ml/l |
| iron solution | sol mère | 2 ml/l |

Heat sterilized together in demi water

After Sterilization

|  |  |  |
|---|---|---|
| biotin solution | sol mère | 1 ml/l |
| CaCO$_3$ |  | 4 g/l |

Standard Medium+Complete Vits/OE Solutions+FE×1 w/o Urea

|  |  | concentration g/L |
|---|---|---|
| potassium dihydrogen phosphate | KH$_2$PO$_4$ | 1.5 |
| magnesium sulphate | MgSO$_4$•7H$_2$O | 0.5 |
| antimousse | erol 18 | 0.1 ml/l |
| OE solution | sol mère | 1 ml/l |
| iron solution | sol mère | 1 ml/l |

Heat sterilized together in demi water

After Sterilization

|  |  |  |
|---|---|---|
| Vitamins solution* | sol mère | 1 ml/l |
| CaCO$_3$ |  | 4 g/l |

Standard Medium+Complete Vits/OE Solutions+Fe×1

|  |  | concentration g/L |
|---|---|---|
| urée | CH$_4$N$_2$O | 1 |
| potassium dihydrogen phosphate | KH$_2$PO$_4$ | 1.5 |
| magnesium sulphate | MgSO$_4$•7H$_2$O | 0.5 |
| antimousse | erol 18 | 0.1 ml/l |
| OE solution | sol mère | 1 ml/l |
| iron solution | sol mère | 1 ml/l |

Heat sterilized together in demi water

After Sterilization

|  |  |  |
|---|---|---|
| Vitamins solution* | sol mère | 1 ml/l |
| CaCO$_3$ |  | 4 g/l |

OE Stock Solution

|  |  | conc sol mère g/kg |
|---|---|---|
| Ethylenediaminetetraacetic acide dihydrate (EDTA) | C$_{10}$H$_{14}$N$_2$Na$_2$O$_6$•2H$_2$O | 15.00 |
| Zinc sulfate heptahydrate | ZnSO$_4$•7H$_2$O | 4.50 |
| Magnanese chloride tetrahydrate | MnCl$_2$•4H$_2$O | 0.84 |
| Cobalt chloride hexahydrate | CoCl$_2$•6H$_2$O | 0.30 |
| Copper (II) sulfate pentahydrate | CuSO$_4$•5H$_2$O | 0.30 |
| Sodium molybdate dihydrate | Na$_2$MoO$_4$•2H$_2$O | 0.40 |
| Calcium chloride dihydrate | CaCl$_2$•2H$_2$O | 4.50 |
| Fer sulfate heptahydrate | FeSO$_4$•7H$_2$O | 3.00 |
| Boric acid | H$_3$BO$_3$ | 1.00 |
| Potassium iodide | KI | 0.10 |

Iron Stock Solution

|  |  | conc sol mère g/kg |
|---|---|---|
| Ethylenediaminetetraacetic acid dihydrate (EDTA) | C$_{10}$H$_{14}$N$_2$Na$_2$O$_6$•2H$_2$O | 15.00 |
| Fer sulfate heptahydrate | FeSO$_4$•7H$_2$O | 3.00 |

Vitamins Stock Solution

|  |  | conc sol mère g/L |
|---|---|---|
| Biotine (TLC) (vitamine B7) | C$_{10}$H$_{16}$N$_2$SO$_3$ | 0.05 |
| D-Pantothenic acid hemicalcium salt (vitamine B5) | C$_9$H$_{16}$NO$_5$ | 1 |
| Nicotinic acid (vitamine B3) | C$_6$H$_6$NO$_2$ | 1 |
| Myo-inositol | C$_6$H$_{12}$O$_6$ | 25 |
| Thiamine hydrochloride (vitamine B1) | C$_{12}$H$_{17}$ClN$_4$SO | 1 |
| Pyridoxine hydrochloride (Vitamine B6) | C$_8$H$_{11}$NO$_3$•HCl | 1 |
| p-Aminobenzoic acid (PABA) | C$_7$H$_7$NO$_2$ | 0.2 |

Biotin Stock Solution

|  |  | conc sol mère g/L |
|---|---|---|
| Biotine (TLC) (vitamine B7) | C$_{10}$H$_{16}$N$_2$SO$_3$ | 1 |

---

The invention claimed is:

1. A process for the production of succinic acid comprising fermenting yeast cells in a vessel comprising a first suitable fermentation medium, wherein at least a portion of the yeast cells are reused in a second suitable fermentation medium, wherein the second suitable fermentation medium is the first suitable fermentation medium further supplemented with a vitamin and a trace element, wherein the vitamin is one or more B complex vitamins selected from the group consisting of a $B_1$ vitamin, a $B_2$ vitamin, a $B_3$ vitamin, a $B_5$ vitamin, a $B_6$ vitamin, a $B_7$ vitamin, a $B_8$ vitamin, a $B_9$ vitamin, a $B_{12}$ vitamin, and a $B_x$ vitamin, and wherein the trace element is one or more of iron, cobalt, copper, zinc, manganese, molybdenum, iodine, selenium, boron, chromium, arsenic, or silicon.

2. A process according to claim 1, wherein the reuse comprises withdrawing yeast cells from the vessel and adding the withdrawn yeast cells back to the same vessel or to a second vessel comprising the second suitable fermentation medium.

3. A process according to claim 1, wherein the vitamin is a $B_1$ vitamin, a $B_3$ vitamin, a $B_5$ vitamin, a $B_6$ vitamin, a $B_7$ vitamin, a $B_8$ vitamin, and a $B_x$ vitamin.

4. A process according to claim 1, wherein the trace element is a combination of zinc, manganese, cobalt, copper, molybdenum, iron and boron.

5. A process according to claim 1, wherein the yeast cell is a yeast belonging to *Saccharomyces cerevisiae*.

6. A process according to claim 1, wherein the east cell is a genetically modified yeast cell comprising insertion of a gene selected from the group consisting of a gene encoding a pyruvate carboxylase, a phosphoenolpyruvate carboxykinase, a malate dehydrogenase, a fumarase, a fumarate reductase, an isocitrate lyase, a malate synthase and a dicarboxylic acid transporter.

7. A process according to claim 1, wherein the succinic acid is recovered from the fermentation medium.

8. A process according to claim 1, wherein multiple recycle steps are carried out, optionally two or three recycle steps.

9. A process according to claim 6, wherein the gene is a gene encoding a dicarboxylic acid transporter and wherein the dicarboxylic acid transporter is the malic acid transporter of SEQ ID NO: 5.

10. A process for increasing specific productivity of a dicarboxylic acid in a production strain during recycling of the strain comprising:
   a) fermenting the production strain in a first fermentation medium in a fermentation vessel;
   b) withdrawing at least a portion of the production strain from the fermentation vessel;
   c) introducing the portion of the production strain obtained in b) into the same fermentation vessel or into a second fermentation vessel containing a second fermentation medium;
   d) fermenting the portion of the production strain in the second fermentation medium; and optionally
   e) recovering the dicarboxylic acid from the first and/or second fermentation medium;

wherein the production strain is a yeast strain;
   wherein the dicarboxylic acid is selected from the group consisting of succinic acid, fumaric acid, malic acid, and adipic acid;
   wherein the second fermentation medium consists of the first fermentation medium, a vitamin solution, and a trace element solution;
   wherein the vitamin solution comprises vitamin $B_7$ (biotin), vitamin $B_5$ (pantothenic acid), vitamin $B_3$ (niacin), vitamin $B_8$ (myo-inositol), vitamin $B_1$ (thiamine), vitamin $B_6$ (pyridoxine hydrochloride), and vitamin $B_x$ (p-aminobenzoic acid); and
   wherein the trace element solution comprises ethylenediaminetetraacetic acid dehydrate (EDTA), zinc, manganese, cobalt, copper, molybdenum, calcium, iron, boron, and iodine.

11. A process according to claim 10, wherein the yeast strain is *Saccharomyces cerevisiae*.

12. A process according to claim 10, wherein the yeast strain is a genetically modified yeast strain comprising insertion of a gene selected from the group consisting of a gene encoding a pyruvate carboxylase, a phosphoenolpyruvate carboxykinase, a malate dehydrogenase, a fumarase, a fumarate reductase, an isocitrate lyase, a malate synthase and a dicarboxylic acid transporter.

13. A process according to claim 12, wherein the gene is a gene encoding a dicarboxylic acid transporter and wherein the dicarboxylic acid transporter is the malic acid transporter of SEQ ID NO: 5.

14. A process according to claim 10, wherein the dicarboxylic acid is succinic acid.

15. A process according to claim 10, wherein the specific productivity (qp) of the dicarboxylic acid during the fermentation of step d) is the same as or greater than the specific productivity (qp) of the dicarboxylic acid during the fermentation of step a).

* * * * *

SEQUENCE LISTING

<160> NUMBER OF SEQ ID NOS: 5

<210> SEQ ID NO 1
<211> LENGTH: 538
<212> TYPE: PRT
<213> ORGANISM: Artificial Sequence
<220> FEATURE:
<223> OTHER INFORMATION: Actinobacillus succinogenes phosphoenolpyruvate
      carboxykinase amino acid sequence, with EGY to DAF modification at
      pos 120 - 122.

<400> SEQUENCE: 1

```
Met Thr Asp Leu Asn Lys Leu Val Lys Glu Leu Asn Asp Leu Gly Leu
1               5                   10                  15
Thr Asp Val Lys Glu Ile Val Tyr Asn Pro Ser Tyr Glu Gln Leu Phe
            20                  25                  30
Glu Glu Glu Thr Lys Pro Gly Leu Glu Gly Phe Asp Lys Gly Thr Leu
        35                  40                  45
Thr Thr Leu Gly Ala Val Ala Val Asp Thr Gly Ile Phe Thr Gly Arg
    50                  55                  60
Ser Pro Lys Asp Lys Tyr Ile Val Cys Asp Glu Thr Thr Lys Asp Thr
65                  70                  75                  80
Val Trp Trp Asn Ser Glu Ala Ala Lys Asn Asp Asn Lys Pro Met Thr
                85                  90                  95
Gln Glu Thr Trp Lys Ser Leu Arg Glu Leu Val Ala Lys Gln Leu Ser
            100                 105                 110
Gly Lys Arg Leu Phe Val Val Asp Ala Phe Cys Gly Ala Ser Glu Lys
        115                 120                 125
His Arg Ile Gly Val Arg Met Val Thr Glu Val Ala Trp Gln Ala His
    130                 135                 140
Phe Val Lys Asn Met Phe Ile Arg Pro Thr Asp Glu Glu Leu Lys Asn
145                 150                 155                 160
Phe Lys Ala Asp Phe Thr Val Leu Asn Gly Ala Lys Cys Thr Asn Pro
                165                 170                 175
Asn Trp Lys Glu Gln Gly Leu Asn Ser Glu Asn Phe Val Ala Phe Asn
            180                 185                 190
Ile Thr Glu Gly Ile Gln Leu Ile Gly Gly Thr Trp Tyr Gly Gly Glu
        195                 200                 205
Met Lys Lys Gly Met Phe Ser Met Met Asn Tyr Phe Leu Pro Leu Lys
    210                 215                 220
Gly Val Ala Ser Met His Cys Ser Ala Asn Val Gly Lys Asp Gly Asp
225                 230                 235                 240
Val Ala Ile Phe Phe Gly Leu Ser Gly Thr Gly Lys Thr Thr Leu Ser
                245                 250                 255
Thr Asp Pro Lys Arg Gln Leu Ile Gly Asp Asp Glu His Gly Trp Asp
            260                 265                 270
Glu Ser Gly Val Phe Asn Phe Glu Gly Gly Cys Tyr Ala Lys Thr Ile
        275                 280                 285
Asn Leu Ser Gln Glu Asn Glu Pro Asp Ile Tyr Gly Ala Ile Arg Arg
    290                 295                 300
Asp Ala Leu Leu Glu Asn Val Val Arg Ala Asp Gly Ser Val Asp
305                 310                 315                 320
Phe Asp Asp Gly Ser Lys Thr Glu Asn Thr Arg Val Ser Tyr Pro Ile
                325                 330                 335
Tyr His Ile Asp Asn Ile Val Arg Pro Val Ser Lys Ala Gly His Ala
            340                 345                 350
Thr Lys Val Ile Phe Leu Thr Ala Asp Ala Phe Gly Val Leu Pro Pro
        355                 360                 365
Val Ser Lys Leu Thr Pro Glu Gln Thr Glu Tyr Phe Leu Ser Gly
    370                 375                 380
Phe Thr Ala Lys Leu Ala Gly Thr Glu Arg Gly Val Thr Glu Pro Thr
385                 390                 395                 400
Pro Thr Phe Ser Ala Cys Phe Gly Ala Ala Phe Leu Ser Leu His Pro
                405                 410                 415
```

```
Ile Gln Tyr Ala Asp Val Leu Val Glu Arg Met Lys Ala Ser Gly Ala
            420                 425                 430

Glu Ala Tyr Leu Val Asn Thr Gly Trp Asn Gly Thr Gly Lys Arg Ile
            435                 440                 445

Ser Ile Lys Asp Thr Arg Gly Ile Ile Asp Ala Ile Leu Asp Gly Ser
            450                 455                 460

Ile Glu Lys Ala Glu Met Gly Glu Leu Pro Ile Phe Asn Leu Ala Ile
465                 470                 475                 480

Pro Lys Ala Leu Pro Gly Val Asp Pro Ala Ile Leu Asp Pro Arg Asp
                    485                 490                 495

Thr Tyr Ala Asp Lys Ala Gln Trp Gln Val Lys Ala Glu Asp Leu Ala
            500                 505                 510

Asn Arg Phe Val Lys Asn Phe Val Lys Tyr Thr Ala Asn Pro Glu Ala
            515                 520                 525

Ala Lys Leu Val Gly Ala Gly Pro Lys Ala
            530                 535
```

<210> SEQ ID NO 2
<211> LENGTH: 1139
<212> TYPE: PRT
<213> ORGANISM: Artificial Sequence
<220> FEATURE:
<223> OTHER INFORMATION: Glycosomal Trypanosoma brucei fumarate
      reductase (FRDg) amino acid sequence lacking 3 aa C-terminal
      targeting signal.

<400> SEQUENCE: 2

```
Met Val Asp Gly Arg Ser Ser Ala Ser Ile Val Ala Val Asp Pro Glu
1               5                   10                  15

Arg Ala Ala Arg Glu Arg Asp Ala Ala Arg Ala Leu Leu Gln Asp
            20                  25                  30

Ser Pro Leu His Thr Thr Met Gln Tyr Ala Thr Ser Gly Leu Glu Leu
            35                  40                  45

Thr Val Pro Tyr Ala Leu Lys Val Val Ala Ser Ala Asp Thr Phe Asp
            50                  55                  60

Arg Ala Lys Glu Val Ala Asp Glu Val Leu Arg Cys Ala Trp Gln Leu
65                  70                  75                  80

Ala Asp Thr Val Leu Asn Ser Phe Asn Pro Asn Ser Glu Val Ser Leu
            85                  90                  95

Val Gly Arg Leu Pro Val Gly Gln Lys His Gln Met Ser Ala Pro Leu
            100                 105                 110

Lys Arg Val Met Ala Cys Cys Gln Arg Val Tyr Asn Ser Ser Ala Gly
            115                 120                 125

Cys Phe Asp Pro Ser Thr Ala Pro Val Ala Lys Ala Leu Arg Glu Ile
            130                 135                 140

Ala Leu Gly Lys Glu Arg Asn Asn Ala Cys Leu Glu Ala Leu Thr Gln
145                 150                 155                 160

Ala Cys Thr Leu Pro Asn Ser Phe Val Ile Asp Phe Glu Ala Gly Thr
            165                 170                 175

Ile Ser Arg Lys His Glu His Ala Ser Leu Asp Leu Gly Gly Val Ser
            180                 185                 190

Lys Gly Tyr Ile Val Asp Tyr Val Ile Asp Asn Ile Asn Ala Ala Gly
            195                 200                 205

Phe Gln Asn Val Phe Phe Asp Trp Gly Gly Asp Cys Arg Ala Ser Gly
            210                 215                 220
```

-continued

```
Met Asn Ala Arg Asn Thr Pro Trp Val Val Gly Ile Thr Arg Pro Pro
225                 230                 235                 240

Ser Leu Asp Met Leu Pro Asn Pro Pro Lys Glu Ala Ser Tyr Ile Ser
            245                 250                 255

Val Ile Ser Leu Asp Asn Glu Ala Leu Ala Thr Ser Gly Asp Tyr Glu
        260                 265                 270

Asn Leu Ile Tyr Thr Ala Asp Lys Pro Leu Thr Cys Thr Tyr Asp
            275                 280                 285

Trp Lys Gly Lys Glu Leu Met Lys Pro Ser Gln Ser Asn Ile Ala Gln
290                 295                 300

Val Ser Val Lys Cys Tyr Ser Ala Met Tyr Ala Asp Ala Leu Ala Thr
305                 310                 315                 320

Ala Cys Phe Ile Lys Arg Asp Pro Ala Lys Val Arg Gln Leu Leu Asp
            325                 330                 335

Gly Trp Arg Tyr Val Arg Asp Thr Val Arg Asp Tyr Arg Val Tyr Val
        340                 345                 350

Arg Glu Asn Glu Arg Val Ala Lys Met Phe Glu Ile Ala Thr Glu Asp
            355                 360                 365

Ala Glu Met Arg Lys Arg Ile Ser Asn Thr Leu Pro Ala Arg Val
370                 375                 380

Ile Val Val Gly Gly Gly Leu Ala Gly Leu Ser Ala Ala Ile Glu Ala
385                 390                 395                 400

Ala Gly Cys Gly Ala Gln Val Val Leu Met Glu Lys Glu Ala Lys Leu
            405                 410                 415

Gly Gly Asn Ser Ala Lys Ala Thr Ser Gly Ile Asn Gly Trp Gly Thr
            420                 425                 430

Arg Ala Gln Ala Lys Ala Ser Ile Val Asp Gly Gly Lys Tyr Phe Glu
            435                 440                 445

Arg Asp Thr Tyr Lys Ser Gly Ile Gly Gly Asn Thr Asp Pro Ala Leu
            450                 455                 460

Val Lys Thr Leu Ser Met Lys Ser Ala Asp Ala Ile Gly Trp Leu Thr
465                 470                 475                 480

Ser Leu Gly Val Pro Leu Thr Val Leu Ser Gln Leu Gly Gly His Ser
                485                 490                 495

Arg Lys Arg Thr His Arg Ala Pro Asp Lys Lys Asp Gly Thr Pro Leu
            500                 505                 510

Pro Ile Gly Phe Thr Ile Met Lys Thr Leu Glu Asp His Val Arg Gly
            515                 520                 525

Asn Leu Ser Gly Arg Ile Thr Ile Met Glu Asn Cys Ser Val Thr Ser
530                 535                 540

Leu Leu Ser Glu Thr Lys Glu Arg Pro Asp Gly Thr Lys Gln Ile Arg
545                 550                 555                 560

Val Thr Gly Val Glu Phe Thr Gln Ala Gly Ser Gly Lys Thr Thr Ile
                565                 570                 575

Leu Ala Asp Ala Val Ile Leu Ala Thr Gly Gly Phe Ser Asn Asp Lys
            580                 585                 590

Thr Ala Asp Ser Leu Leu Arg Glu His Ala Pro His Leu Val Asn Phe
            595                 600                 605

Pro Thr Thr Asn Gly Pro Trp Ala Thr Gly Asp Gly Val Lys Leu Ala
        610                 615                 620

Gln Arg Leu Gly Ala Gln Leu Val Asp Met Asp Lys Val Gln Leu His
625                 630                 635                 640
```

-continued

Pro Thr Gly Leu Ile Asn Pro Lys Asp Pro Ala Asn Pro Thr Lys Phe
            645                 650                 655

Leu Gly Pro Glu Ala Leu Arg Gly Ser Gly Gly Val Leu Leu Asn Lys
        660                 665                 670

Gln Gly Lys Arg Phe Val Asn Glu Leu Asp Leu Arg Ser Val Val Ser
        675                 680                 685

Lys Ala Ile Met Glu Gln Gly Ala Glu Tyr Pro Gly Ser Gly Gly Ser
690                 695                 700

Met Phe Ala Tyr Cys Val Leu Asn Ala Ala Gln Lys Leu Phe Gly
705                 710                 715                 720

Val Ser Ser His Glu Phe Tyr Trp Lys Lys Met Gly Leu Phe Val Lys
                725                 730                 735

Ala Asp Thr Met Arg Asp Leu Ala Ala Leu Ile Gly Cys Pro Val Glu
                740                 745                 750

Ser Val Gln Gln Thr Leu Glu Glu Tyr Glu Arg Leu Ser Ile Ser Gln
                755                 760                 765

Arg Ser Cys Pro Ile Thr Arg Lys Ser Val Tyr Pro Cys Val Leu Gly
        770                 775                 780

Thr Lys Gly Pro Tyr Tyr Val Ala Phe Val Thr Pro Ser Ile His Tyr
785                 790                 795                 800

Thr Met Gly Gly Cys Leu Ile Ser Pro Ser Ala Glu Ile Gln Met Lys
                805                 810                 815

Asn Thr Ser Ser Arg Ala Pro Leu Ser His Ser Asn Pro Ile Leu Gly
                820                 825                 830

Leu Phe Gly Ala Gly Glu Val Thr Gly Gly Val His Gly Gly Asn Arg
        835                 840                 845

Leu Gly Gly Asn Ser Leu Leu Glu Cys Val Val Phe Gly Arg Ile Ala
    850                 855                 860

Gly Asp Arg Ala Ser Thr Ile Leu Gln Arg Lys Ser Ser Ala Leu Ser
865                 870                 875                 880

Phe Lys Val Trp Thr Thr Val Leu Arg Glu Val Arg Glu Gly Gly
                885                 890                 895

Val Tyr Gly Ala Gly Ser Arg Val Leu Arg Phe Asn Leu Pro Gly Ala
                900                 905                 910

Leu Gln Arg Ser Gly Leu Ser Leu Gly Gln Phe Ile Ala Ile Arg Gly
        915                 920                 925

Asp Trp Asp Gly Gln Gln Leu Ile Gly Tyr Tyr Ser Pro Ile Thr Leu
    930                 935                 940

Pro Asp Asp Leu Gly Met Ile Asp Ile Leu Ala Arg Ser Asp Lys Gly
945                 950                 955                 960

Thr Leu Arg Glu Trp Ile Ser Ala Leu Glu Pro Gly Asp Ala Val Glu
                965                 970                 975

Met Lys Ala Cys Gly Gly Leu Val Ile Glu Arg Arg Leu Ser Asp Lys
                980                 985                 990

His Phe Val Phe Met Gly His Ile Ile Asn Lys Leu Cys Leu Ile Ala
        995                 1000                1005

Gly Gly Thr Gly Val Ala Pro Met Leu Gln Ile Ile Lys Ala Ala
    1010                1015                1020

Phe Met Lys Pro Phe Ile Asp Thr Leu Glu Ser Val His Leu Ile
    1025                1030                1035

Tyr Ala Ala Glu Asp Val Thr Glu Leu Thr Tyr Arg Glu Val Leu
    1040                1045                1050

```
Glu Glu Arg Arg Arg Glu Ser Arg Gly Lys Phe Lys Lys Thr Phe
    1055                1060                1065

Val Leu Asn Arg Pro Pro Pro Leu Trp Thr Asp Gly Val Gly Phe
    1070                1075                1080

Ile Asp Arg Gly Ile Leu Thr Asn His Val Gln Pro Pro Ser Asp
    1085                1090                1095

Asn Leu Leu Val Ala Ile Cys Gly Pro Pro Val Met Gln Arg Ile
    1100                1105                1110

Val Lys Ala Thr Leu Lys Thr Leu Gly Tyr Asn Met Asn Leu Val
    1115                1120                1125

Arg Thr Val Asp Glu Thr Glu Pro Ser Gly Ser
    1130                1135
```

<210> SEQ ID NO 3
<211> LENGTH: 472
<212> TYPE: PRT
<213> ORGANISM: Artificial Sequence
<220> FEATURE:
<223> OTHER INFORMATION: Rhizopus oryzae fumarase amino acid sequence, lacking the first 23 N-terminal amino acids.

<400> SEQUENCE: 3

```
Met Ser Ser Ala Ser Ala Ala Leu Gln Lys Phe Arg Ala Glu Arg Asp
1               5                   10                  15

Thr Phe Gly Asp Leu Gln Val Pro Ala Asp Arg Tyr Trp Gly Ala Gln
            20                  25                  30

Thr Gln Arg Ser Leu Gln Asn Phe Asp Ile Gly Gly Pro Thr Glu Arg
        35                  40                  45

Met Pro Glu Pro Leu Ile Arg Ala Phe Gly Val Leu Lys Lys Ala Ala
    50                  55                  60

Ala Thr Val Asn Met Thr Tyr Gly Leu Asp Pro Lys Val Gly Glu Ala
65                  70                  75                  80

Ile Gln Lys Ala Ala Asp Glu Val Ile Asp Gly Ser Leu Ile Asp His
                85                  90                  95

Phe Pro Leu Val Val Trp Gln Thr Gly Ser Gly Thr Gln Thr Lys Met
            100                 105                 110

Asn Val Asn Glu Val Ile Ser Asn Arg Ala Ile Glu Leu Leu Gly Gly
        115                 120                 125

Glu Leu Gly Ser Lys Ala Pro Val His Pro Asn Asp His Val Asn Met
    130                 135                 140

Ser Gln Ser Ser Asn Asp Thr Phe Pro Thr Ala Met His Val Ala Ala
145                 150                 155                 160

Val Val Glu Ile His Gly Arg Leu Ile Pro Ala Leu Thr Thr Leu Arg
                165                 170                 175

Asp Ala Leu Gln Ala Lys Ser Ala Glu Phe Glu His Ile Ile Lys Ile
            180                 185                 190

Gly Arg Thr His Leu Gln Asp Ala Thr Pro Leu Thr Leu Gly Gln Glu
        195                 200                 205

Phe Ser Gly Tyr Thr Gln Gln Leu Thr Tyr Gly Ile Ala Arg Val Gln
    210                 215                 220

Gly Thr Leu Glu Arg Leu Tyr Asn Leu Ala Gln Gly Gly Thr Ala Val
225                 230                 235                 240

Gly Thr Gly Leu Asn Thr Arg Lys Gly Phe Asp Ala Lys Val Ala Glu
                245                 250                 255

Ala Ile Ala Ser Ile Thr Gly Leu Pro Phe Lys Thr Ala Pro Asn Lys
            260                 265                 270
```

```
Phe Glu Ala Leu Ala Ala His Asp Ala Leu Val Glu His Gly Ala
            275                 280                 285
Leu Asn Thr Val Ala Cys Ser Leu Met Lys Ile Ala Asn Asp Ile Arg
        290                 295                 300
Tyr Leu Gly Ser Gly Pro Arg Cys Gly Leu Gly Glu Leu Ser Leu Pro
305                 310                 315                 320
Glu Asn Glu Pro Gly Ser Ser Ile Met Pro Gly Lys Val Asn Pro Thr
            325                 330                 335
Gln Cys Glu Ala Met Thr Met Val Cys Ala Gln Val Met Gly Asn Asn
        340                 345                 350
Thr Ala Ile Ser Val Ala Gly Ser Asn Gly Gln Phe Glu Leu Asn Val
            355                 360                 365
Phe Lys Pro Val Met Ile Lys Asn Leu Ile Gln Ser Ile Arg Leu Ile
        370                 375                 380
Ser Asp Ala Ser Ile Ser Phe Thr Lys Asn Cys Val Val Gly Ile Glu
385                 390                 395                 400
Ala Asn Glu Lys Lys Ile Ser Ser Ile Met Asn Glu Ser Leu Met Leu
                405                 410                 415
Val Thr Ala Leu Asn Pro His Ile Gly Tyr Asp Lys Ala Ala Lys Cys
            420                 425                 430
Ala Lys Lys Ala His Lys Glu Gly Thr Thr Leu Lys Glu Ala Ala Leu
        435                 440                 445
Ser Leu Gly Tyr Leu Thr Ser Glu Glu Phe Asp Gln Trp Val Arg Pro
            450                 455                 460
Glu Asp Met Ile Ser Ala Lys Asp
465                 470

<210> SEQ ID NO 4
<211> LENGTH: 340
<212> TYPE: PRT
<213> ORGANISM: Artificial Sequence
<220> FEATURE:
<223> OTHER INFORMATION: Saccharomyces cerevisiae peroxisomal malate
      dehydrogenase (Mdh3) amino acid sequence, lacking the 3 C-terminal
      peroxisomal targeting sequence (SKL).

<400> SEQUENCE: 4

Met Val Lys Val Ala Ile Leu Gly Ala Ser Gly Gly Val Gly Gln Pro
1               5                   10                  15
Leu Ser Leu Leu Leu Lys Leu Ser Pro Tyr Val Ser Glu Leu Ala Leu
            20                  25                  30
Tyr Asp Ile Arg Ala Ala Glu Gly Ile Gly Lys Asp Leu Ser His Ile
        35                  40                  45
Asn Thr Asn Ser Ser Cys Val Gly Tyr Asp Lys Asp Ser Ile Glu Asn
    50                  55                  60
Thr Leu Ser Asn Ala Gln Val Val Leu Ile Pro Ala Gly Val Pro Arg
65                  70                  75                  80
Lys Pro Gly Leu Thr Arg Asp Asp Leu Phe Lys Met Asn Ala Gly Ile
                85                  90                  95
Val Lys Ser Leu Val Thr Ala Val Gly Lys Phe Ala Pro Asn Ala Arg
            100                 105                 110
Ile Leu Val Ile Ser Asn Pro Val Asn Ser Leu Val Pro Ile Ala Val
        115                 120                 125
Glu Thr Leu Lys Lys Met Gly Lys Phe Lys Pro Gly Asn Val Met Gly
    130                 135                 140
```

```
Val Thr Asn Leu Asp Leu Val Arg Ala Glu Thr Phe Leu Val Asp Tyr
145                 150                 155                 160

Leu Met Leu Lys Asn Pro Lys Ile Gly Gln Glu Gln Asp Lys Thr Thr
            165                 170                 175

Met His Arg Lys Val Thr Val Ile Gly Gly His Ser Gly Glu Thr Ile
                180                 185                 190

Ile Pro Ile Ile Thr Asp Lys Ser Leu Val Phe Gln Leu Asp Lys Gln
            195                 200                 205

Tyr Glu His Phe Ile His Arg Val Gln Phe Gly Gly Asp Glu Ile Val
        210                 215                 220

Lys Ala Lys Gln Gly Ala Gly Ser Ala Thr Leu Ser Met Ala Phe Ala
225                 230                 235                 240

Gly Ala Lys Phe Ala Glu Glu Val Leu Arg Ser Phe His Asn Glu Lys
                245                 250                 255

Pro Glu Thr Glu Ser Leu Ser Ala Phe Val Tyr Leu Pro Gly Leu Lys
            260                 265                 270

Asn Gly Lys Lys Ala Gln Gln Leu Val Gly Asp Asn Ser Ile Glu Tyr
        275                 280                 285

Phe Ser Leu Pro Ile Val Leu Arg Asn Gly Ser Val Val Ser Ile Asp
290                 295                 300

Thr Ser Val Leu Glu Lys Leu Ser Pro Arg Glu Gln Leu Val Asn
305                 310                 315                 320

Thr Ala Val Lys Glu Leu Arg Lys Asn Ile Glu Lys Gly Lys Ser Phe
                325                 330                 335

Ile Leu Asp Ser
            340

<210> SEQ ID NO 5
<211> LENGTH: 438
<212> TYPE: PRT
<213> ORGANISM: Schizosaccharomyces pombe
<220> FEATURE:
<221> NAME/KEY: MISC_FEATURE
<222> LOCATION: (1)..(438)
<223> OTHER INFORMATION: Malate permease amino acid sequence

<400> SEQUENCE: 5

Met Gly Glu Leu Lys Glu Ile Leu Lys Gln Arg Tyr His Glu Leu Leu
1               5                   10                  15

Asp Trp Asn Val Lys Ala Pro His Val Pro Leu Ser Gln Arg Leu Lys
            20                  25                  30

His Phe Thr Trp Ser Trp Phe Ala Cys Thr Met Ala Thr Gly Gly Val
        35                  40                  45

Gly Leu Ile Ile Gly Ser Phe Pro Phe Arg Phe Tyr Gly Leu Asn Thr
    50                  55                  60

Ile Gly Lys Ile Val Tyr Ile Leu Gln Ile Phe Leu Phe Ser Leu Phe
65                  70                  75                  80

Gly Ser Cys Met Leu Phe Arg Phe Ile Lys Tyr Pro Ser Thr Ile Lys
                85                  90                  95

Asp Ser Trp Asn His His Leu Glu Lys Leu Phe Ile Ala Thr Cys Leu
            100                 105                 110

Leu Ser Ile Ser Thr Phe Ile Asp Met Leu Ala Ile Tyr Ala Tyr Pro
        115                 120                 125

Asp Thr Gly Glu Trp Met Val Trp Val Ile Arg Ile Leu Tyr Tyr Ile
    130                 135                 140
```

-continued

```
Tyr Val Ala Val Ser Phe Ile Tyr Cys Val Met Ala Phe Phe Thr Ile
145             150             155             160

Phe Asn Asn His Val Tyr Thr Ile Glu Thr Ala Ser Pro Ala Trp Ile
                165             170             175

Leu Pro Ile Phe Pro Pro Met Ile Cys Gly Val Ile Ala Gly Ala Val
            180             185             190

Asn Ser Thr Gln Pro Ala His Gln Leu Lys Asn Met Val Ile Phe Gly
        195             200             205

Ile Leu Phe Gln Gly Leu Gly Phe Trp Val Tyr Leu Leu Leu Phe Ala
    210             215             220

Val Asn Val Leu Arg Phe Phe Thr Val Gly Leu Ala Lys Pro Gln Asp
225             230             235             240

Arg Pro Gly Met Phe Met Phe Val Gly Pro Pro Ala Phe Ser Gly Leu
            245             250             255

Ala Leu Ile Asn Ile Ala Arg Gly Ala Met Gly Ser Arg Pro Tyr Ile
            260             265             270

Phe Val Gly Ala Asn Ser Ser Glu Tyr Leu Gly Phe Val Ser Thr Phe
            275             280             285

Met Ala Ile Phe Ile Trp Gly Leu Ala Ala Trp Cys Tyr Cys Leu Ala
290             295             300

Met Val Ser Phe Leu Ala Gly Phe Phe Thr Arg Ala Pro Leu Lys Phe
305             310             315             320

Ala Cys Gly Trp Phe Ala Phe Ile Phe Pro Asn Val Gly Phe Val Asn
            325             330             335

Cys Thr Ile Glu Ile Gly Lys Met Ile Asp Ser Lys Ala Phe Gln Met
            340             345             350

Phe Gly His Ile Ile Gly Val Ile Leu Cys Ile Gln Trp Ile Leu Leu
            355             360             365

Met Tyr Leu Met Val Arg Ala Phe Leu Val Asn Asp Leu Cys Tyr Pro
    370             375             380

Gly Lys Asp Glu Asp Ala His Pro Pro Lys Pro Asn Thr Gly Val
385             390             395             400

Leu Asn Pro Thr Phe Pro Pro Glu Lys Ala Pro Ala Ser Leu Glu Lys
            405             410             415

Val Asp Thr His Val Thr Ser Thr Gly Gly Glu Ser Asp Pro Pro Ser
            420             425             430

Ser Glu His Glu Ser Val
            435
```